United States Patent
Hao et al.

(10) Patent No.: US 12,336,738 B2
(45) Date of Patent: Jun. 24, 2025

(54) INTERNAL FIXATION SYSTEM FOR ANATOMICAL REDUCTION OF FRACTURED VERTEBRAL BODY OF SPINE AND INTRAVERTEBRAL BONE GRAFTING

(71) Applicant: Dingjun Hao, Shaanxi (CN)

(72) Inventors: Dingjun Hao, Shaanxi (CN); Haiping Zhang, Shaanxi (CN)

(73) Assignee: Dingjun Hao, Shaanxi (CN)

( * ) Notice: Subject to any disclaimer, the term of this patent is extended or adjusted under 35 U.S.C. 154(b) by 0 days.

(21) Appl. No.: 17/848,435

(22) Filed: Jun. 24, 2022

(65) Prior Publication Data
US 2023/0121328 A1    Apr. 20, 2023

(30) Foreign Application Priority Data
Oct. 15, 2021   (CN) .......................... 202111205607.X

(51) Int. Cl.
*A61B 17/70* (2006.01)
*A61B 17/68* (2006.01)
*A61B 17/56* (2006.01)

(52) U.S. Cl.
CPC ........ *A61B 17/683* (2013.01); *A61B 17/7005* (2013.01); *A61B 17/7014* (2013.01); *A61B 2017/564* (2013.01)

(58) Field of Classification Search
CPC ............ A61B 17/683; A61B 2017/564; A61B 2017/681; A61B 17/7005; A61B 17/7014; A61B 17/7038; A61B 17/7041
See application file for complete search history.

(56) References Cited

U.S. PATENT DOCUMENTS 5,290,288 A * 3/1994 Vignaud ............ A61B 17/7007
606/292
5,533,825 A * 7/1996 Stone ...................... F01D 5/026
74/462

(Continued)

FOREIGN PATENT DOCUMENTS

CN    2553757 Y    6/2003
CN    2553758 Y    6/2003
(Continued)

OTHER PUBLICATIONS

First Office Action dated Apr. 10, 2024 received in corresponding patent family application No. CN202111205607.X. English translation attached.

*Primary Examiner* — Ellen C Hammond

(57) ABSTRACT

The present disclosure discloses an internal fixation system for anatomical reduction of a fractured vertebral body of a spine and intravertebral bone grafting. The system includes at least two injured vertebra nails, each of the at least two injured vertebra nails has a reduction connecting clip connected thereto, and all reduction connecting clips are connected by a connecting rod; the reduction connecting clip includes a fixation screw, a reduction connecting nut, and a reduction connecting screw head; and the reduction connecting screw head and the reduction connecting nut are connected to each other and have a one-way gear structure at a joint thereof. The present disclosure maximizes the recovery and maintenance of an effective height of an injured vertebral body, reduces occurrences of postoperative vertebral body collapses and kyphosis, and decreases fractures of pedicle screw nails and the connecting rod.

8 Claims, 7 Drawing Sheets

(56) References Cited

U.S. PATENT DOCUMENTS

| | | | | |
|---|---|---|---|---|
| 6,128,969 | A * | 10/2000 | Litvin | F16H 1/125 |
| | | | | 74/462 |
| 2005/0187548 | A1 | 8/2005 | Butler et al. | |
| 2006/0167455 | A1* | 7/2006 | Clement | A61B 17/7037 |
| | | | | 606/264 |
| 2011/0196425 | A1* | 8/2011 | Rezach | A61B 17/7035 |
| | | | | 606/246 |
| 2011/0251646 | A1* | 10/2011 | Karnezis | A61B 17/7001 |
| | | | | 606/279 |
| 2012/0303062 | A1* | 11/2012 | Amstutz | A61B 17/7002 |
| | | | | 606/267 |
| 2016/0262740 | A1* | 9/2016 | May | A61B 17/7014 |
| 2016/0270825 | A1* | 9/2016 | Wentz | A61B 17/7016 |
| 2018/0161069 | A1* | 6/2018 | DiPaola | A61B 17/7041 |
| 2020/0040951 | A1* | 2/2020 | Howe | F16D 59/00 |

FOREIGN PATENT DOCUMENTS

| | | |
|---|---|---|
| CN | 101601606 A | 12/2009 |
| CN | 102743216 A | 10/2012 |
| CN | 103932772 A | 7/2014 |
| CN | 106308909 A | 1/2017 |
| CN | 111493990 A | 8/2020 |
| CN | 216221617 U | 4/2022 |

* cited by examiner

INTERNAL FIXATION SYSTEM FOR ANATOMICAL REDUCTION OF FRACTURED VERTEBRAL BODY OF SPINE AND INTRAVERTEBRAL BONE GRAFTING

FIELD

The present disclosure relates to the field of surgical instrument technologies for spinal fractures, and in particular, to an internal fixation system for anatomical reduction of a fractured vertebral body of a spine and intravertebral bone grafting.

BACKGROUND

With the rapid development of the real estate industry, transportation industry, and agriculture, the incidence of accidents remains high, and the incidence of spinal fractures, which have a high disability rate, is on the rise. Most fractures require surgical treatment. At present, for the treatment of spinal fractures, the typical clinical operation is posterior pedicle screw nail fixation, the principle of which is that after a pedicle screw nail is placed, under axial traction by a connecting rod, intervertebral discs above and below an injured vertebra and bone fragments connected to anterior and posterior longitudinal ligaments are rearranged and the shape of the injured vertebra is restored, thereby obtaining a satisfactory vertebral body height.

However, it is difficult to achieve ideal load distribution requirements of the anterior and middle parts of the injured vertebra only through the posterior pedicle screw nail. Also, since the cortex of the injured vertebra and the trabecular bone in the vertebral body are compressed and fractured to varying degrees, for most patients with spinal fractures, a cavity, clinically known as "eggshell-like degeneration", is often formed inside the vertebral body after the height of the vertebral body is restored. Because of this defect, another loss is generated after a correction height of the fracture is restored, thus fracture nonunion, loss of vertebral body height, progressive kyphosis, and intractable lumbago and back pain are likely to occur, and even serious consequences such as an internal fixation breakage, which require revision surgery, are prone to occur. Bone grafting for the anterior and middle parts of a burst vertebral body through the injured vertebra pedicle can effectively solve the problem of the hollow vertebral body, provide relatively stable internal support for the fractured vertebral body, and provide good conditions for fracture healing. Therefore, bionics of restoring the shape of the injured vertebra and bionics of mechanics and motion by means of reconstructing the injured vertebra through bone grafting in the injured vertebra are hot topics of research in the past 10 years.

At present, we have found that for clinically-applied spinal fracture reduction systems, the reduction principle of which is to obtain the height of the injured vertebra by preflexing connecting rods on left and right sides of the injured vertebra, or by stretching pedicle nails of the connecting rods upwardly and downwardly. Regardless of a degree of preflexing or a distance of stretching, the operator has to constantly loosen a nut of each pedicle screw nail to re-install and re-fasten the pedicle screw, and thus repeated adjustments are required, which prolong exposure time of the patient during the operation and increases the risk of infection and bleeding. In addition, the main problem is that when the bone grafting is performed on the injured vertebra by passing through the pedicle to fill the bone loss, it was found that the connecting rods on the two sides blocked a passage of the bone grafting through the pedicle. Some scholars used the connecting rod on one side for reduction and support, and performed the bone grafting through the pedicle on an opposite side. Such a method of unilateral reduction leads to a limited height of the vertebral body, and also, the stress applied on the injured vertebra is uneven. Reducing steps during a surgery on the premise of obtaining satisfactory reduction of the injured vertebra while performing adequate bone grafting on the bone loss site in the injured vertebra has become the key to solving the clinical problem.

SUMMARY

In order to solve problems existing in the related art, the present disclosure provides an internal fixation system for anatomical reduction of a fractured vertebral body of a spine and intravertebral bone grafting. The present disclosure maximizes the recovery and maintenance of an effective height of an injured vertebral body, reduces occurrences of postoperative vertebral body collapses and kyphosis, and decreases fractures of pedicle screw nails and the connecting rod.

In order to achieve the above objectives, the present disclosure provides the following technical solutions.

An internal fixation system for anatomical reduction of a fractured vertebral body of a spine and intravertebral bone grafting is provided. The system includes at least two injured vertebra nails. Each of the at least two injured vertebra nails has a reduction connecting clip connected thereto, and all reduction connecting clips are connected by a connecting rod. The reduction connecting clip includes a fixation screw, a reduction connecting nut, and a reduction connecting screw head; the reduction connecting nut has a connection through hole and a fixation screw hole, and an end of the reduction connecting rod is configured to extend into the connection through hole; the fixation screw is configured to be thread-connected to the fixation screw hole to fix the reduction connecting rod; and the reduction connecting screw head has a connecting hole, and an upper end of the injured vertebra nail is configured to extend into and be fixed in the connecting hole. The reduction connecting screw head and the reduction connecting nut are connected to each other and have a one-way gear structure at a joint thereof, and the reduction connecting screw head and the reduction connecting nut are rotatable in one direction relative to each other.

As a further improvement of the present disclosure, each of the at least two injured vertebra nails includes a connecting screw head, an intermediate nut, and an insert screw that are connected in sequence; and the connecting screw head is configured to be inserted into the connecting hole and to be thread-connected to a connecting nut for fixation.

As a further improvement of the present disclosure, the connecting screw head further has a break-off groove defined thereon.

As a further improvement of the present disclosure, the reduction connecting screw head further has a limiting groove defined on a side thereof opposite to the connecting hole, and the limiting groove is in communication with the connecting hole; and the connecting nut is configured to be arranged in the limiting groove.

As a further improvement of the present disclosure, the limiting groove and the connecting nut are non-circular structures that match each other.

As a further improvement of the present disclosure, the one-way gear structure includes an inner gear ring arranged on the reduction connecting nut and an outer gear ring arranged on the reduction connecting screw head, and the inner gear ring and the outer gear ring match each other to form a helical gear mechanism.

As a further improvement of the present disclosure, an included angle between two adjacent teeth on each of the inner gear ring and the outer gear ring and a center is 3°.

As a further improvement of the present disclosure, the reduction connecting nut has an inner hole defined therein along an axial direction, the inner hole is in communication with the connection through hole and the fixation screw hole, the inner gear ring is arranged on one side of the inner hole, and the inner gear ring has a limiting ring provided on an outer edge thereof.

As a further improvement of the present disclosure, one end of the reduction connecting screw head is a gear end, the outer gear ring is arranged on the gear end, the other end of the reduction connecting screw head is a limiting end, the connecting hole is arranged on the limiting end, and a diameter of the limiting end is smaller than a diameter of the gear end and is smaller than an inner diameter of the limiting ring.

As a further improvement of the present disclosure, the fixation screw is a hollow cylindrical body, and the hollow cylindrical body has an outer thread provided outside and has a tool operating chamber defined inside.

Compared with the related art, the present disclosure can provide the following advantageous effects.

For the internal fixation system for the anatomical reduction of the fractured vertebral body of the spine and the intravertebral bone grafting of the present disclosure, since the reduction connecting rod is connected to two injured vertebra nails through the reduction connecting clips, the reduction connecting rod and the two injured vertebra nails are not on one straight line. Therefore, when the connecting rod in the reduction system is located on an outer side during an operation, stimulation and interference to capsules of superior and inferior zygapophyseal joints are reduced, the joint capsules are effectively protected, and postoperative pains and degeneration of the zygapophyseal joints are alleviated. The reduction system adopts the connecting clips for automatic reduction, which ensures the recovery of the height of the injured vertebra, also has advantages of allowing intravertebral bone grafting: (1) enhancing the support for the vertebral body by applying an effective filler; (2) improving stability of anterior and middle parts of the injured vertebra; (3) effectively lowering the risk of eggshell-like changes; and (4) avoiding a re-loss of the height of the injured vertebra, effectively reduces occurrences of adjacent segment disease (ASD) when the reduction connecting rod is located on an outer side, and bypasses a needle entry position at the pedicle of the injured vertebra when the reduction connecting rod is located on an inner side, and during the operation, and allows intravertebral reinforcement or bone grafting by passing through the pedicle, thereby maximizing the recovery and maintenance of the effective height of the injured vertebral body, reducing the occurrences of postoperative vertebral body collapses and kyphosis, and decreasing the fractures of pedicle screw nails and the connecting rod.

Further, instead of relying on a conventional preflexed connecting rod, or relying on the lever principle of injured vertebra nails and stretching of superior and inferior connecting rods for reduction, the reduction principle of the system implements reduction through the automatic reduction connecting clips. The reduction connecting clip is designed as a rotatable one-way gear structure, and an angle formed between the injured vertebra nail and the connecting rod is 3° each time the reduction connecting clip is adjusted upwardly or downwardly. Therefore, during the operation, automatic adjustments can be made based on different degrees of fractures, until the fracture reduction is satisfactory, thereby reducing degree estimations of a flex rod, shortening time for repeatedly disassembling a screw plug and adjusting the flex rod, and avoiding a possibility of bone nonunion due to excessive separation of the fractured end resulted from overstretch in pursuit of reduction.

BRIEF DESCRIPTION OF DRAWINGS

The drawings described herein are for explanatory purposes only and are not intended to limit the scope of the present disclosure in any way. In addition, shapes and proportions of components in the figures are merely schematic and are used to facilitate understanding of the present disclosure, rather than specifically limit the shapes and proportions of the components in the present disclosure. In the drawings.

DESCRIPTION OF EMBODIMENTS

In order to provide better understanding of technical solutions of the present disclosure for those skilled in the art, the technical solutions according to the embodiments of the present disclosure will be clearly and completely described below with reference to the accompanying drawings in the embodiments of the present disclosure. Apparently, the embodiments described below are only some of the embodiments of the present disclosure, but not all of the embodiments. On a basis of the embodiments in the present disclosure, all other embodiments obtained by those of ordinary skill in the art without creative labor shall fall within the protection scope of the present disclosure.

It should be noted that when an element is referred to as being "disposed on" another element, it can be directly on another element, or an intermediate element may also be present. When one element is referred to as being "connected" to another element, it can be directly connected to another element, or an intermediate element may also be present. Terms "vertical", "horizontal", "left", "right", and similar expressions used herein are for the purpose of illustration only and do not indicate a unique embodiment.

Unless otherwise defined, all technical and scientific terms used herein have the same meaning as commonly understood by those skilled in the art to which the present disclosure belongs. The terms used herein in the description of the present disclosure are for the purpose of describing specific embodiments merely, and are not intended to limit the present disclosure. As used herein, the term "and/or" includes any and all combinations of one or more associated listed items.

Figure 1:
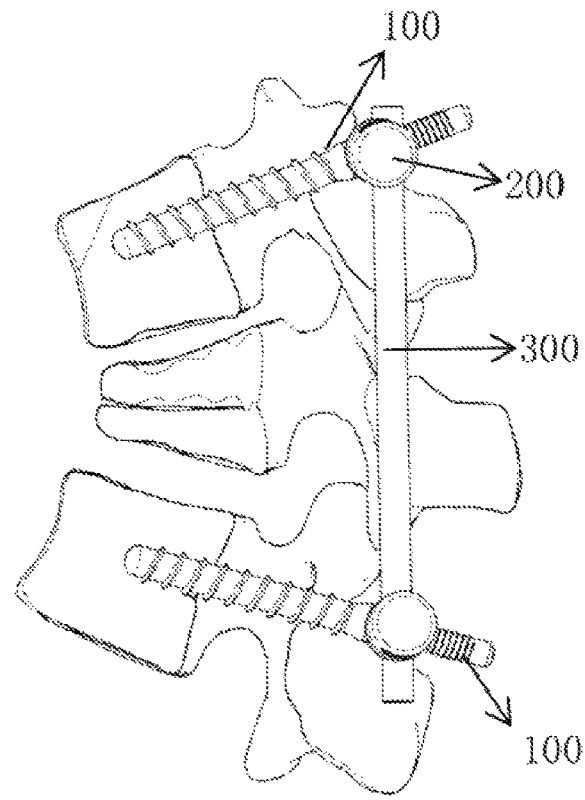
FIG. 1 is a schematic diagram of an internal fixation system for anatomical reduction of a fractured vertebral body of a spine and intravertebral bone grafting.
Figure 2:
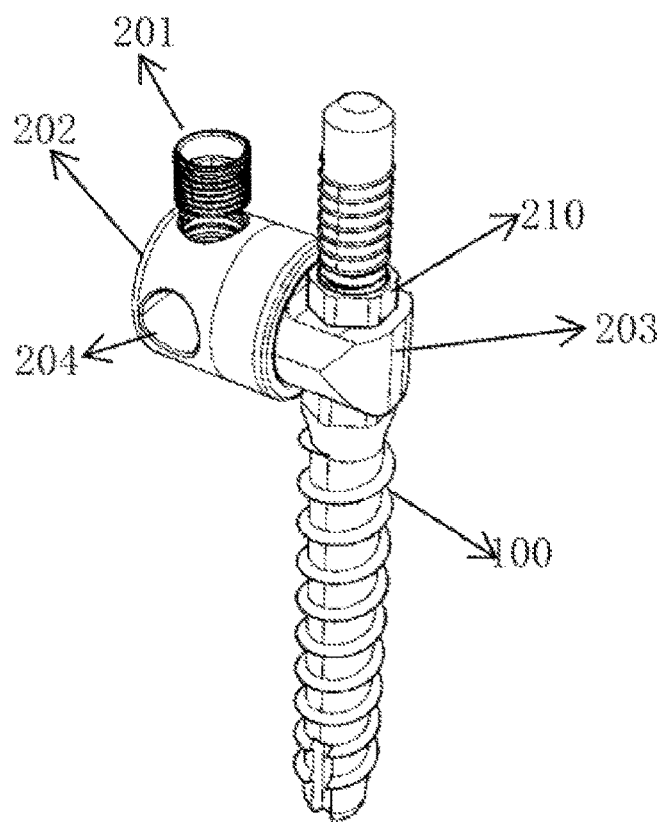
FIG. 2 is a partial schematic diagram of an internal fixation system for anatomical reduction of a fractured vertebral body of a spine and intravertebral bone grafting.

As illustrated in FIG. 1 and FIG. 2, the present disclosure provides an internal fixation system for anatomical reduction of a fractured vertebral body of a spine and intravertebral bone grafting. The system includes at least two injured vertebra nails 100. Each of the at least two injured vertebra nails 100 has a reduction connecting clip 200 connected thereto, and all reduction connecting clips 200 are connected by a connecting rod 300. The reduction connecting clip 200 includes a fixation screw 201, a reduction connecting nut 202, and a reduction connecting screw head 203; the reduction connecting nut 202 has a connection through hole 204 and a fixation screw hole 209, and an end of the reduction connecting rod 300 is configured to extend into the connection through hole 204; the fixation screw 201 is configured to be thread-connected to the fixation screw hole 209 to fix the reduction connecting rod 300; and the reduction connecting screw head 203 has a connecting hole 205, and an upper end of the injured vertebra nail 100 is configured to extend into and be fixed in the connecting hole 205. The reduction connecting screw head 203 and the reduction connecting nut 202 are connected to each other and have a one-way gear structure at a joint thereof, and the reduction connecting screw head 203 and the reduction connecting nut 202 are rotatable in one direction relative to each other.

Since the reduction connecting rod 300 is connected to two injured vertebra nails 100 through the reduction connecting clips 200, the reduction connecting rod 300 and the two injured vertebra nails 100 are not on one straight line. Therefore, when the connecting rod in the reduction system is located on an outer side during an operation, stimulation and interference to capsules of superior and inferior zygapophyseal joints are reduced. Therefore, the articular capsules are effectively protected, and postoperative pains and degeneration of zygapophyseal joints are alleviated.

Figure 3:
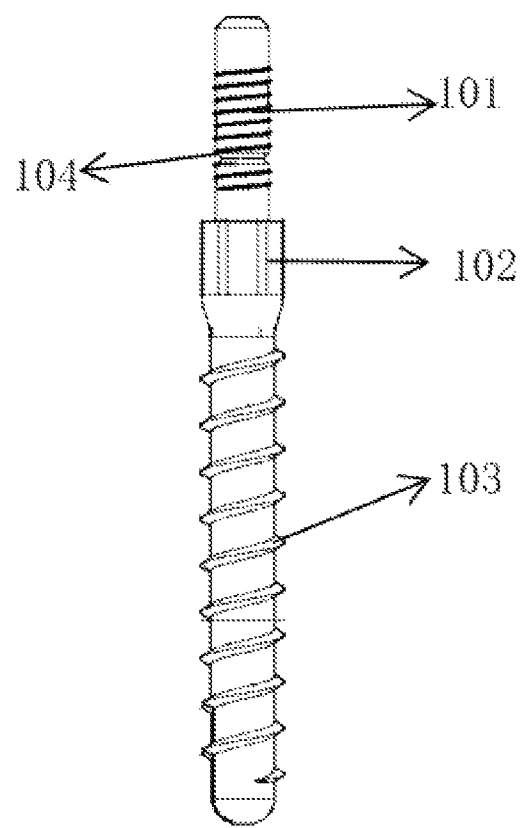
FIG. 3 is a schematic diagram of an injured vertebra nail.

Specifically, as illustrated in FIG. 3, the injured vertebra nail 100 includes a connecting screw head 101, an intermediate nut 102, and an insert screw 103 that are connected in sequence; and the connecting screw head 101 is configured to be inserted into the connecting hole 205 and to be thread-connected to a connecting nut 210 for fixation.

Here, the connecting screw head 101 further has a break-off groove 104 defined thereon. The break-off groove 104 divides a thread on the connecting screw head 101 into upper and lower parts. A function of the break-off groove 104 is that when a protruding end affects the operation, an unwanted part can be broken off through the break-off groove 104.

Figure 4:
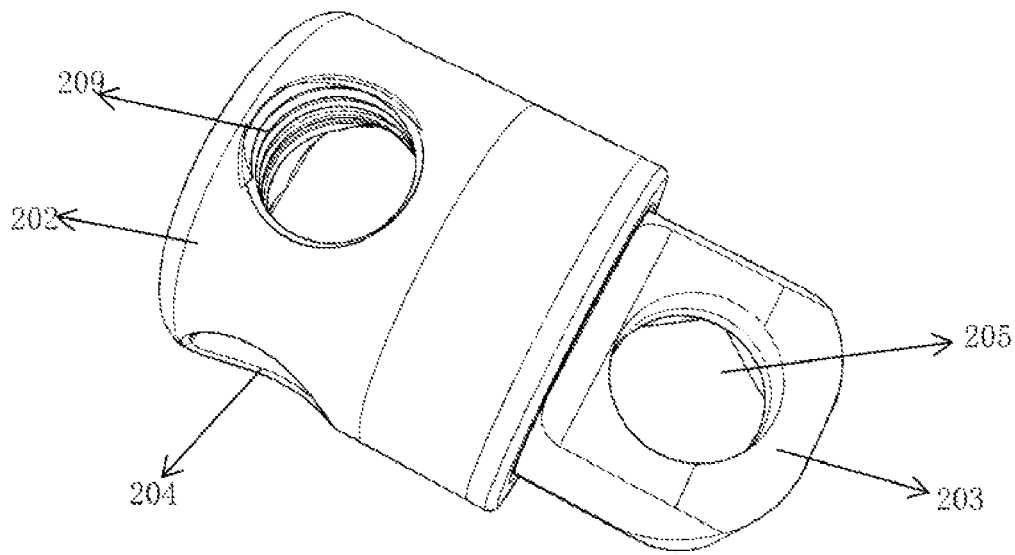
FIG. 4 is a schematic diagram of a reduction connecting clip.
Figure 5:
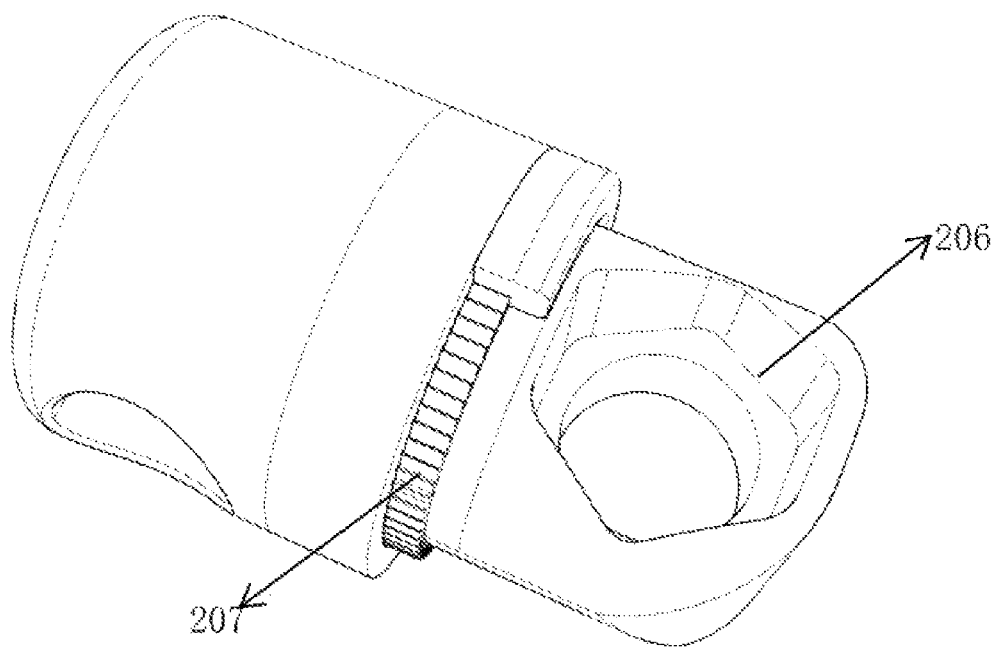
FIG. 5 is a schematic diagram of a reduction connecting clip observed from another angle.

As illustrated in FIG. 4 and FIG. 5, the reduction connecting screw head 203 further has a limiting groove 206 defined on a side thereof opposite to the connecting hole 205, and the limiting groove 206 is in communication with the connecting hole 205; and the connecting nut 210 is configured to be arranged in the limiting groove 206.

The limiting groove 206 and the connecting nut 210 are non-circular structures that match each other. In a preferred embodiment of the present disclosure, the non-circular structure has a regular hexagon shape. The connecting nut 210 is hexagonal outside. The limiting groove 206 is hexagonal inside. Of course, the non-circular structure is not limited to any of these examples, and other trigonal, tetragonal, pentagonal, or irregular shapes can also be used.

Figure 6:
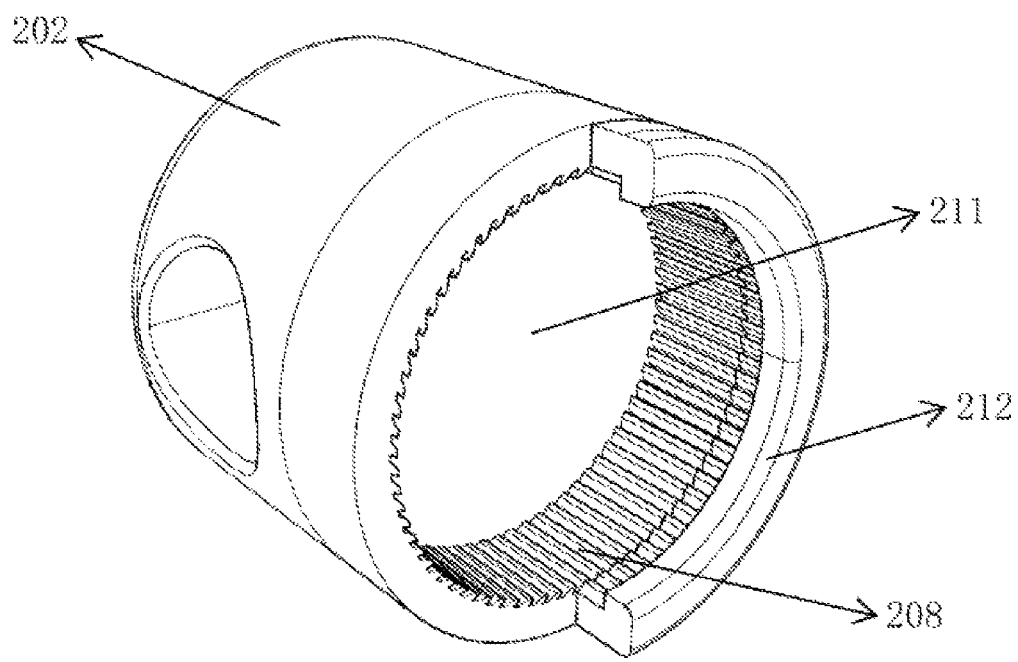
FIG. 6 is a schematic diagram of a reduction connecting nut.
Figure 7:
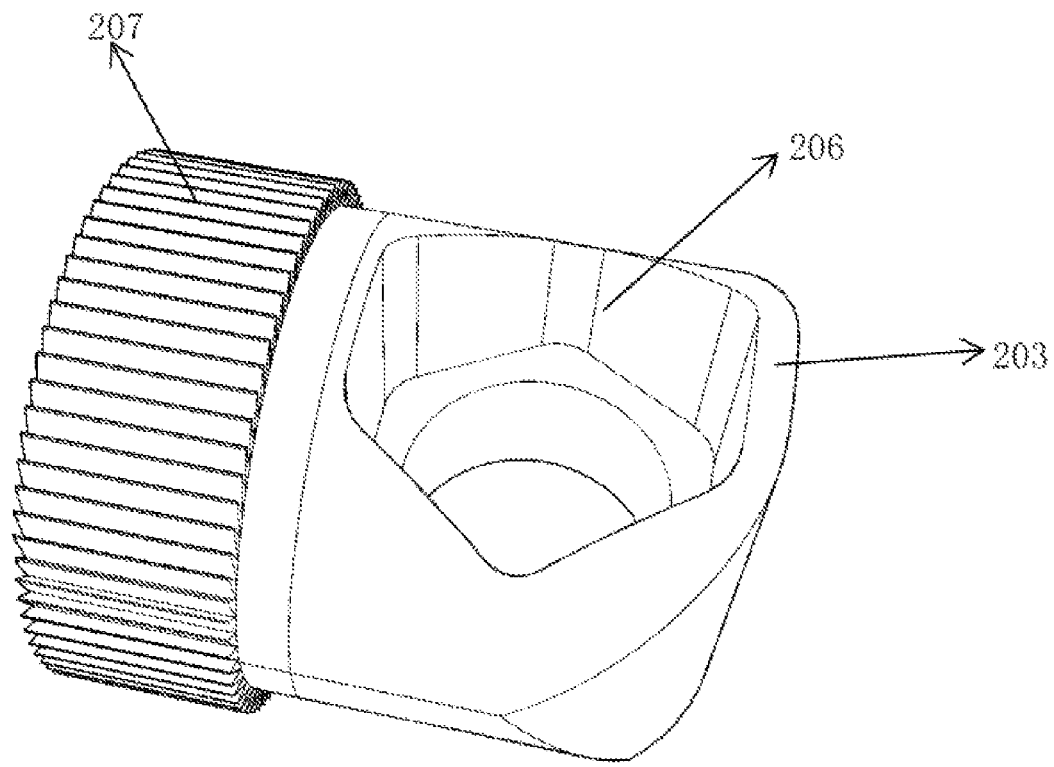
FIG. 7 is a schematic diagram of a reduction connecting screw head.
Figure 8:
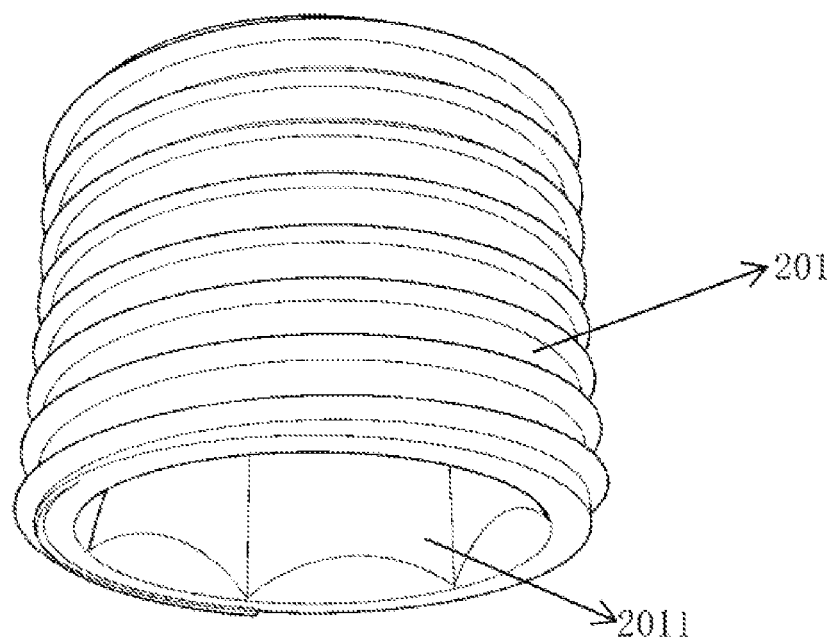
FIG. 8 is a schematic diagram of a fixation screw.
Figure 9:
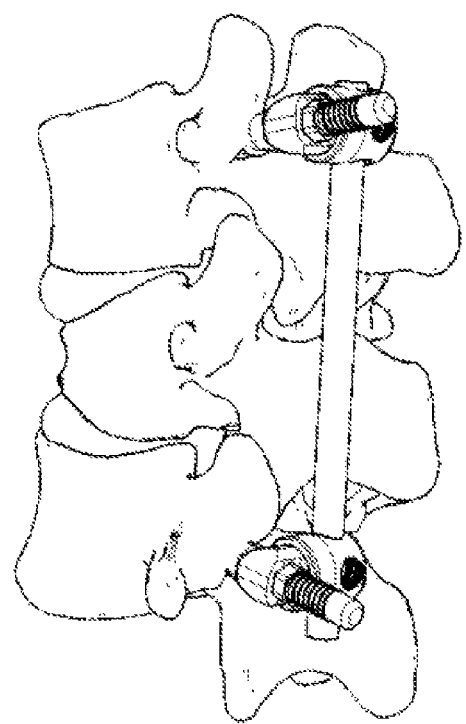
FIG. 9 is a first schematic diagram showing a use state according to the present disclosure.
Figure 10:
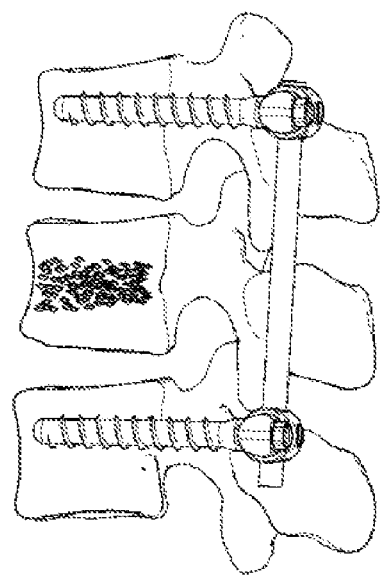
FIG. 10 is a second schematic diagram showing a use state according to the present disclosure.
Figure 11:
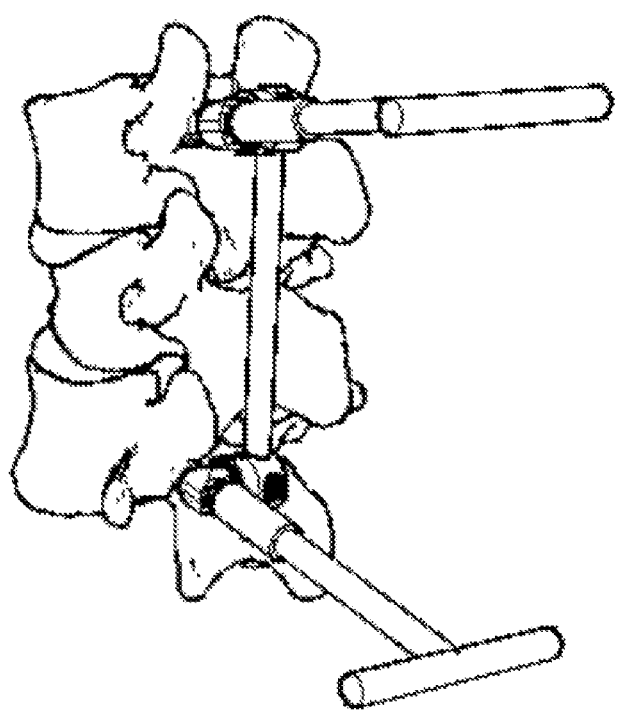
FIG. 11 is a third schematic diagram showing a use state according to the present disclosure.

As illustrated in FIG. 5 to FIG. 7, the one-way gear structure includes an inner gear ring 208 arranged on the reduction connecting nut 202 and an outer gear ring 207 arranged on the reduction connecting screw head 203, and the inner gear ring 208 and the outer gear ring 207 match each other to form a helical gear mechanism.

In a preferred embodiment, an included angle between two adjacent teeth on each of the inner gear ring 208 and the outer gear ring 207 and a center is 3°. When it is necessary to adjust an angle of each of the two injured vertebra nails 100, a 3° adjustment can be selectively realized by adjusting a gear through the one-way gear structure.

Preferably, as illustrated in FIG. 6, the reduction connecting nut 202 has an inner hole 211 defined therein along an axial direction thereof, the inner hole 211 is in communication with the connection through hole 204 and the fixation screw hole 209, the inner gear ring 208 is arranged on one side of the inner hole 211, and the inner gear ring 208 has a limiting ring 212 provided on an outer edge thereof. When a connection is required, the reduction connecting screw head 203 is passed through the inner hole 211 of the reduction connecting nut 202, the inner gear ring 208 and the outer gear ring 207 are engaged with each other, and the limiting ring 212 prevents the reduction connecting screw head 203 from sliding out of the reduction connecting nut 202.

Specifically, one end of the reduction connecting screw head 203 is a gear end, the outer gear ring 207 is arranged on the gear end, the other end of the reduction connecting screw head 203 is a limiting end, the connecting hole 205 is arranged on the limiting end, and a diameter of the limiting end is smaller than a diameter of the gear end and is smaller than an inner diameter of the limiting ring 212.

The fixation screw 201 is a hollow cylindrical body, the hollow cylindrical body has an outer thread provided outside and has a tool operating chamber 2011 defined inside. The tool operating chamber 2011 can be, for example, hexagonal inside, which is convenient for operations of a hexagonal wrench. The fixation screw 20 adopts a built-in structure, which has no protruding part after being screwed tight, and thus does not interfere with operations during a surgery.

FIG. 9 to FIG. 13 are schematic diagrams showing use processes according to the present disclosure. Referring to FIG. 9 to FIG. 13, processes of a surgery are as follows.

After a successful implementation of anesthesia, a patient was placed in a prone position having the abdomen of the patient suspended, followed by routine disinfection and drape.

A median longitudinal incision was made by taking a spinous process of a diseased vertebra as a center. The skin and subcutaneous tissues were incised layer by layer to the thoracolumbar dorsal fascia, and were stripped from left and right approaches of the spinous process to expose the vertebral lamina until the zygapophyseal joints. Superior and inferior articular capsules were protected, an entry point of each pedicle screw nail was determined. After nail passages that passed through pedicles on both sides were prepared for vertebral bodies above and below the injured vertebra with a mouth gag, pedicle screw nails were inserted into the passages and reduction connecting clips were mounted. A connecting rod of an appropriate length was measured and mounted on upper and lower reduction clips, and screw plugs were screwed. A special reduction tool was used to establish a connection to a tail end of each pedicle screw nail. Rear compression and automatic reduction were performed with the connecting clip as a central axis. When it was confirmed, by means of C-arm perspective, that the height of the injured vertebra was restored, the reduction was stopped and the screw plugs were tightened. Then, a bone grafting funnel was placed through the pedicles on both sides of the injured vertebrae to perform bone grafting for filling an "eggshell cavity" inside the injured vertebra. After C-arm perspective showed satisfactory fracture reduction, the bone grafting funnel was removed, the pedicle screw nail passages were capped with bone wax. After rinsing with massive normal saline and strict hemostasis, instruments and gauzes were checked without error, and after a drainage tube was placed, the incisions were closed layer by layer. After wrapping, the surgery ended.

Figure 12:
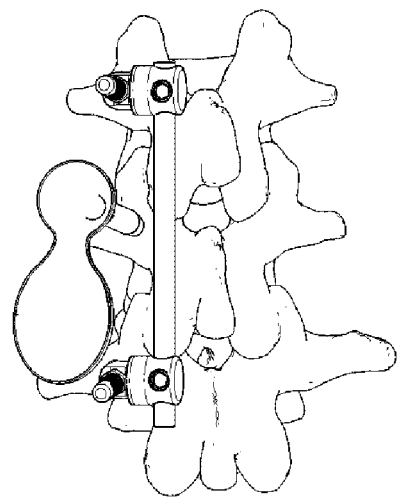
FIG. 12 is a fourth schematic diagram showing a use state according to the present disclosure.
Figure 13:
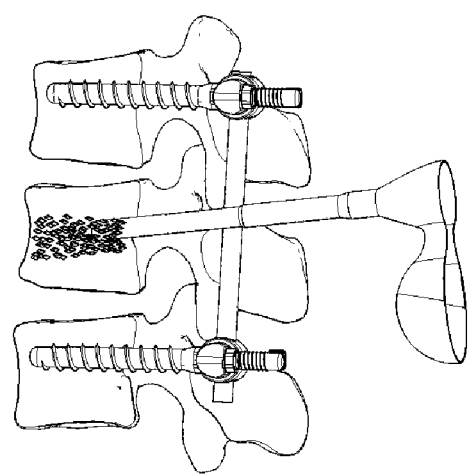
FIG. 13 is a fifth schematic diagram showing a use state according to the present disclosure.

Here, it can be clearly seen in FIG. 12 that the connecting rod does not block implantation of the bone grafting funnel for the injured vertebra.

A needle entry position at the pedicle of the injured vertebra is bypassed when the reduction connecting rod is located on an inner side. During an operation, intravertebral reinforcement or bone grafting can be carried out by passing through the pedicle, thereby maximizing the recovery and maintenance of the effective height of the injured vertebral body, reducing the occurrences of postoperative vertebral body collapses and kyphosis, and decreasing the fractures of pedicle screw nails and the connecting rod.

Instead of relying on a conventional preflexed connecting rod, or relying on the lever principle of injured vertebra nails and stretching of upper and lower connecting rods for reduction, the reduction principle of the system implements reduction through the automatic reduction connecting clip. The reduction connecting clip is designed as a rotatable one-way gear structure, and an angle formed between the injured vertebra nail and the connecting rod is 3° each time the reduction connecting clip is adjusted upwardly or downwardly. In this way, during the operation, automatic adjustments can be made based on different degrees of fractures, until the fracture reduction is satisfactory, thereby reducing degree estimations of a flex rod, shortening time for repeatedly disassembling a screw plug and adjusting the flex rod, and avoiding a possibility of bone nonunion due to excessive separation of the fractured end resulted from overstretch in pursuit of reduction.

It should be noted that, in the description of the present disclosure, terms "first", "second", etc., are only used for the purpose of description and to distinguish similar objects. There is no sequential order between the terms, nor can they be construed as indicating or imply relative importance. Also, in the description of the present disclosure, unless otherwise specified, "a plurality of" means two or more.

It should be understood that the above description is for illustration purposes, rather than limitations. From reading the above description, many embodiments and applications beyond the examples provided will be apparent to those skilled in the art. Therefore, the scope of the present teachings, instead of being determined with reference to the above description, should be determined with reference to the scope of the claims as attached, along with equivalents of the claims. All articles and references, including contents of patent applications and publications, are incorporated herein by reference for a purpose of being comprehensive. An omission of any aspect of a subject matter disclosed herein in the claims as attached is not intended to disclaim such subject matter, nor should it be construed the applicant not considering such subject matter as part of the disclosed subject matter of the present disclosure.

What is claimed is:

1. An internal fixation system for anatomical reduction of a fractured vertebral body of a spine and intravertebral bone grafting, comprising at least two injured vertebra nails, wherein each of the at least two injured vertebra nails has a reduction connecting clip connected thereto, and all reduction connecting clips are connected by a connecting rod;

each of the at least two reduction connecting clips comprises a fixation screw, a reduction connecting nut, and a reduction connecting screw head; the reduction connecting nut has a connection through hole and a fixation screw hole, and an end of the reduction connecting rod is configured to extend into the connection through hole; the fixation screw is configured to be thread-connected to the fixation screw hole to fix the reduction connecting rod; and the reduction connecting screw head has a connecting hole, and an upper end of the injured vertebra nail is configured to extend into and be fixed in the connecting hole; and the reduction connecting screw head and the reduction connecting nut are connected to each other and have a one-way gear structure at a joint thereof, and the reduction connecting screw head and the reduction connecting nut are rotatable in one direction relative to each other, wherein the one-way gear structure comprises an inner gear ring arranged on the reduction connecting nut and an outer gear ring arranged on the reduction connecting screw head, and the inner gear ring and the outer gear ring match each other to form a gear mechanism with slanted gear teeth that are all parallel to one another, and a triangular structure is formed by extension lines corresponding to two adjacent ones of the injured vertebra nails and the connecting rod between the two adjacent injured vertebra nails, wherein the reduction connecting nut has an inner hole defined therein along an axial direction, the inner hole is in communication with the connection through hole and the fixation screw hole, the inner gear ring is arranged on one side of the inner hole, and the inner gear ring has a limiting ring provided on an outer edge thereof, the limiting ring extending away from the outer edge of the inner gear ring.

2. The internal fixation system for the anatomical reduction of the fractured vertebral body of the spine and the intravertebral bone grafting according to claim 1, wherein each of the at least two injured vertebra nails comprises a connecting screw head, an intermediate nut, and an insert screw that are connected in sequence; and the connecting screw head is configured to be inserted into the connecting hole and to be thread-connected to a connecting nut for fixation.

3. The internal fixation system for the anatomical reduction of the fractured vertebral body of the spine and the intravertebral bone grafting according to claim 2, wherein the connecting screw head further has a break-off groove defined thereon.

4. The internal fixation system for the anatomical reduction of the fractured vertebral body of the spine and the intravertebral bone grafting according to claim 2, wherein the reduction connecting screw head further has a limiting groove defined on a side thereof opposite to the connecting hole, and the limiting groove is in communication with the connecting hole; and the connecting nut is configured to be arranged in the limiting groove.

5. The internal fixation system for the anatomical reduction of the fractured vertebral body of the spine and the intravertebral bone grafting according to claim 4, wherein the limiting groove and the connecting nut are non-circular structures that match each other.

6. The internal fixation system for the anatomical reduction of the fractured vertebral body of the spine and the intravertebral bone grafting according to claim 1, wherein an included angle between two adjacent teeth on each of the inner gear ring and the outer gear ring and a center is 3°.

7. The internal fixation system for the anatomical reduction of the fractured vertebral body of the spine and the intravertebral bone grafting according to claim 1, wherein one end of the reduction connecting screw head is a gear end, the outer gear ring is arranged on the gear end, the other end of the reduction connecting screw head is a limiting end, the connecting hole is arranged on the limiting end, and a diameter of the limiting end is smaller than a diameter of the gear end and is smaller than an inner diameter of the limiting ring.

8. The internal fixation system for the anatomical reduction of the fractured vertebral body of the spine and the intravertebral bone grafting according to claim 1, wherein the fixation screw is a hollow cylindrical body, and the hollow cylindrical body has an outer thread provided outside and has a tool operating chamber defined inside.

\* \* \* \* \*